United States Patent
Lang (10) Patent No.: US 7,238,379 B2
(45) Date of Patent: Jul. 3, 2007

(54) PROCESS FOR SELECTIVITY EXTRACTING BIOACTIVE COMPONENTS

(75) Inventor: Timothy R. Lang, Pymble (AU)

(73) Assignee: Queen Bioactives Pty Ltd, Queensland (AU)

( * ) Notice: Subject to any disclaimer, the term of this patent is extended or adjusted under 35 U.S.C. 154(b) by 486 days.

(21) Appl. No.: 10/377,729

(22) Filed: Mar. 4, 2003

(65) Prior Publication Data

US 2004/0081734 A1 Apr. 29, 2004

Related U.S. Application Data

(63) Continuation of application No. PCT/AU01/01113, filed on Sep. 4, 2001.

(30) Foreign Application Priority Data

Sep. 4, 2000 (AU) .................................. PQ9874

(51) Int. Cl.
*A33B 4/00* (2006.01)
(52) U.S. Cl. ...................... 426/542; 426/655
(58) Field of Classification Search ................ 426/615, 426/616, 590, 599, 271, 478, 481, 542
See application file for complete search history.

(56) References Cited

U.S. PATENT DOCUMENTS 2,661,907 A 12/1953 Wissmiller
4,352,746 A * 10/1982 Bracco et al. .............. 252/398
5,679,806 A 10/1997 Zheng et al.
5,734,046 A 3/1998 Ifuku et al.
5,817,354 A 10/1998 Mozaffar et al.

FOREIGN PATENT DOCUMENTS

EP 0 657 169 A1 6/1995
WO WO 00/32062 A1 6/2000

OTHER PUBLICATIONS

Nirdosh K. Jagota & Steve F. Cheatham, "HPLC separation of flavonoids and flavonoid glycosides using a polystyrene/divinylbenzene column," Journal of Liquid Chromatography, 15(4):603-15 (1992).

* cited by examiner

*Primary Examiner*—Kamal A. Saeed
(74) *Attorney, Agent, or Firm*—Birch, Stewart, Kolasch & Birch, LLP

(57) ABSTRACT

A process for selectively extracting bioactive components from a raw material extract derived from vegetable matter, including the steps of: (a) passing said raw material extract through a passageway containing an adsorbent whereby at least some of the components to be extracted are adsorbed onto the said adsorbent; (b) subsequently passing through said passageway an eluent mixture substantially containing water and alcohol whereby the concentration of alcohol in the eluent is increased at a substantially constant rate from 15 vol percent to 95 vol percent during at least those periods when the components are being eluted; (c) sequentially collecting an eluate in fractions corresponding to the presence of the extracted components.

11 Claims, 11 Drawing Sheets

PROCESS FOR SELECTIVITY EXTRACTING BIOACTIVE COMPONENTS

This application is a Continuation of copending PCT International Application No. PCT/AU01/01113 filed on Sep. 4, 2001, which was published in English and which designated the United States and on which priority is claimed under 35 U.S.C. § 120, the entire contents of which are hereby incorporated by reference.

FIELD OF THE INVENTION

The invention relates to a process for extracting components from fruits and/or plants. The invention particularly but not exclusively relates to a process for selectively extracting components containing limonoid glucosides, flavanones and polymethoxylated flavones from a raw material composed of citrus juice, citrus molasses and/or peel water. The invention also particularly but not exclusively relates to phenolic acids and hydroxy flavones from a raw material composed of sugar cane. The invention also particularly but not exclusively relates to a process for selectively extracting components respectively containing phenolic acids, proanthocyanidins, hydroxy flavones and flavonois from from a raw material composed of apples and/or potatoes. The invention also particularly but not exclusively relates to a process for selectively extracting components respectively containing flavonois, stilbenes, proanthocyanidins, phenolic acids and anthocyanins from a raw material composed of grapes.

BACKGROUND OF THE INVENTION

Citrus fruits contain a range of compounds which are biologically active in humans. Many of these compounds have a beneficial antioxidant activity with the ability to produce advantageous physiological effects in the treatment of conditions such as cancer, heart disease, high blood pressure and arthritis. For example citrus limonoid compounds derived from citrus may be used as anti-tumour agents. Further studies have also identified beneficial physiological effects produced by Flavonoids such as Flavanones and Polymethoxylated Flavones.

The bioactive compounds present in citrus fruits include groups consisting of Limonoids and Flavonoids.

Limonoids are a group of triterpenoid derivatives found in naturally occurring substances such as citrus fruits. The compounds which typically occur in citrus fruits are linked to a glucose molecule (the glucoside) and are commonly referred to as limonoid glucosides.

Flavonoids being to the group of benzopyrane derivatives which occur widely in nature. They have a typical chemical structure consisting of one benzene ring with a fused heterocyclic six membered ring containing an oxygen atom. These compounds also contain phenolic hydroxyl groups, which may be free, methylated or bound to sugars. Typically, flavonoids are distinguished by means of differences between the heterocyclic rings and between additional functional groups. Three types of flavonoids occur in citrus fruits—flavanones, flavones and flavonois. Many of these exist as glycosides.

Flavonones are the most predomonant type of citrus flavonoid. In fruits such as sweet orange, mandarin and lemon the dominant flavanone is the nearly tasteless hesperidin, while in more bitter fruits such as grapefruit, pummelo and sour orange, the more bitter flavanone naringin dominates.

The term polymethoxylated flavones represents the chemical family of flavones with a number of methoxyl groups equal to or greater than 4. These compounds are almost exclusively found in citrus fruits with a specific characteristic distribution for each variety. They are found in all parts of the fruit including the peel, flavedo, albedo and endocarp.

In the citrus processing industry, a commercial practice has arisen of producing juice or juice additives from citrus peel. In this process water soluble components are extracted from the peel using a range of devices. The resultant extract is typically bitter and astringent due to the large amounts of limonoid and flavonoid compounds which are particularly concentrated in the peel. To ensure the juice is not overly bitter the extract is typically clarified and de-bittered. The de-bittering process involves contacting the extract with a polymer adsorbent. This results in the adsorption on the polymer of some of the bitter principles; the remaining natural sugars, acids and some flavour compounds remain in the treated "juice". This treatment results in the adsorption of a large portion of the flavonoid compounds in addition to the limonoids.

Commercial de-bittering operations typically regenerate the polymer by desorbing the removed compounds with a caustic soda solution. This process destroys the bioactive and flavour components resulting in their discharge as waste with the spent caustic solution, without harnessing these valuable bioactive by-products.

The object of the present invention is to address some or all of these problems, and to effect a separation of individual bioactive components.

SUMMARY OF THE INVENTION

According to the present invention, there is provided a process for selectively extracting bioactive components from a raw material extract derived from vegetable matter, including the steps of:
  (a) passing said raw material extract through a passageway containing an adsorbent whereby at least some of the components to be extracted are adsorbed on to the said adsorbent;
  (b) subsequentially passing through said passageway an eluent mixture substantially containing water and alcohol whereby the concentration of alcohol in the eluent is increased at a substantially constant rate from 15 vol percent to 95 vol percent during at least those periods when the components are being eluted;
  (c) sequentially collecting an eluate in fractions corresponding to the presence of the extracted components.

One embodiment of the present invention in particular provides a process for selectively extracting components respectively containing limonoid glucosides, flavanones, and polymethoxylated flavones from a raw material composed of citrus juice, citrus molasses and/or peel water including the steps of:
  (a) passing said raw material through a passageway containing an adsorbent whereby at least some of the components to be extracted are adsorbed onto the said adsorbent;
  (b) subsequently passing through said passageway an eluent mixture substantially containing water and alcohol wherein the concentration of alcohol in the eluent is increased at a substantially constant rate from 15 vol % to 95 vol % during at least those periods when the components are being eluted;

(c) sequentially collecting an eluate in fractions corresponding to the presence of the extracted components.

Usually, the flavanones extracted are flavanone glycosides.

The present invention also provides processes for selectively extracting components respectively containing phenolic acids and hydroxy flavones from raw material composed of sugar cane; or phenolic acids, proanthocyanidins, hydroxy flavones and flavonoles from raw material composed of apples and/or potatoes; or flavonois, stilbenes, proanthocyanidins, phenolic acids and anthocyanins from raw materials composed from grapes; said process including steps (a) to (c) above.

A further embodiment of the invention provides a process for selectively extracting bioactive components from a raw material extract derived from vegetable matter, including the steps of:

(a) combining said raw material extract with sufficient alcohol to ensure at least one bioactive component will not be adsorbed when the combined raw material extract and alcohol are passed through a first passageway containing adsorbent;

(b) passing said combined raw material extract and alcohol through a first passageway containing an adsorbent whereby at least some of the components to be extracted are adsorbed on to the said adsorbent;

(c) reducing the alcohol component of the combined raw material extract and alcohol to less than 15 vol percent;

(d) passing the combined raw material extract and remaining alcohol through a second passageway containing an adsorbent whereby remaining components to be extracted are adsorbed on to the said adsorbent;

(e) subsequently passing through said first passageway an eluent mixture substantially containing water and alcohol wherein the concentration of alcohol in the eluent is increased at a substantially constant rate from 50 vol percent to 95 vol percent during at least those periods when the components are being eluted.

(f) subsequently passing through said second passageway an eluent mixture substantially containing water and alcohol wherein the concentration of alcohol in the eluent is increased at a substantially constant rate from 15 vol percent to 15 vol percent during at least those periods when the components are being eluted;

(g) sequentially collecting from each passageway an eluent in fractions corresponding to the presence of the bioactive components.

The raw material provided can be in any suitable form. Where components are extracted from citrus fruit this raw material may include extracts from all parts of the fruit. Furthermore, where components are extracted from citrus fruit, a particularly suitable raw material consists of extract from the peel. A high concentration extract from citrus peel may be obtained using counter current extraction of sliced citrus peel with water.

The raw material may also be treated in any suitable manner before being processed by the invention. Processing by centrifuge and/or filtration to minimise the amount of suspended solids in the solution is particularly desirable.

The passageway(s) of the present invention may be provided in any suitable form. This may be provided by packing a column, container, vessel or pipe with adsorbent. A gravity fed packed column is a particularly suitable form of passageway. The column may be packed in any suitable manner with any suitable arrangement of adsorbent beads. Preferably the ratio of the length of the column to its diameter is 4:1 or greater.

The adsorbent may be provided in any suitable form. A particular suitable form for the adsorbent is in the form of beads which can be in any suitable shape and size. Preferably, the adsorbent used is polystyrene-divinyl benzene.

Furthermore, any suitable alcohol may be used to elute the components from the raw material. In a particularly preferred form of the invention, the alcohol is ethanol.

Where alcohol has been combined with the raw material extract so as to ensure at least one bioactive component is not adsorbed during passage through the first passageway, the volume percentage of alcohol in the combined alcohol/raw material extract is reduced to less than 15 vol % prior to passing through the second passageway. This is preferably carried out by removing alcohol from the combined alcohol/raw material extract in an evaporator.

The fractions may be collected in any suitable manner. Any suitable number of fractions may be collected. The collection of fractions may be arranged to maximise the concentration of a desired component in a particular fraction. Preferably, an in-line spectrophotometer is used to detect the presence of specific components in the eluate and indicate suitable fractions.

The concentration of alcohol in the eluent mixture can be increased at any suitable, substantially constant rate whilst the eluate contains the components of interest. The alcohol concentration may be increased from 15 vol % to 45 vol % over a period of approximately 7.5 hours. The alcohol concentration may be increased from 75 vol % to 95 vol % over a period of approximately 5 hours. In a preferred form of the invention, the rate at which the alcohol concentration of the solution is increased is greater between 45 vol % to 75 vol % alcohol, as the components of interest are not eluted over this range.

Where the raw material extract contains more than three bioactive components with a wide range of hydrophobicity, problems may be encountered in separating the components. Recovery of strongly hydrophobic components may result in excessive losses of relatively hydrophilic components.

Accordingly, in a preferred form of the invention, the adsorption step is carried out using two passageways containing adsorbent. Alcohol is added to the raw material extract to a level calculated to ensure that the more hydrophilic components will not be adsorbed by the adsorbent, and the alcohol/raw material extract mixture is passed through a first passageway to adsorb the more hydrophobic components. The more hydrophobic components are then eluated from the first passageway using a water/alcohol eluent as previously described.

The alcohol/raw material extract mixture containing the more hydrophilic components, which are not adsorbed is de-alcoholised to a level where the more hydrophilic components will be adsorbed when in contact with the adsorbent, and is passed through a second passageway for adsorption. The more hydrophilic components are then eluted from the second passageway using a water/alcohol eluent as previously described.

By using this technique it has been found that there is a marginal improvement in the efficiency of separation of bioactive components, and a significant improvement in the capacity of a given volume of polymer adsorbent to load bioactive components without loss of yield.

The process may include the additional step of processing the eluted fractions further by evaporating the alcohol to yield a further concentrated form of the extracted component. The concentrated form of the extracted component may then be freeze dried or incorporated into an oil base for storage, transport or use.

In a particular preferred form of the invention the presence of a particular extracted component in the eluate is detected by an in-line spectrophotometer.

BRIEF DESCRIPTION OF THE DRAWINGS

The invention will now be described in further detail by reference to the enclosed drawings which relate to an example form of the invention. It is to be understood that the particularity of the example and the drawings do not supersede the generality of the preceding description of the invention.

DETAILED DESCRIPTION

In one preferred embodiment of the invention, a multiple stage counter current diffusion extractor is used to separate water soluble juice compounds from water insolubles. The resulting juice is at least partially depectinised, pasteurised and clarified. This may be done with either a self desludging high speed centrifuge or by filtration.

The clarified juice is then contacted with an adsorbent which preferentially adsorbs the limonoid glucosides, flavanones and polymethoxylated flavones. A suitable device for the purposes of effecting contact between the juice is an automated twin column polymer adsorption device.

After a sufficient build up of adsorbed components on the adsorbent, the flow of juice to the adsorbent column is stopped. The column is then fed with a mixture of water and alcohol. This eluent mixture is delivered to the column at a predetermined rate varying between 1 and 5 bed volumes per hour.

The concentration of alcohol in the eluent is increased until it reaches approximately 15% vol alcohol. The concentration of alcohol in the eluent is increased at a substantially constant rate until the alcohol concentration in the entering solution reaches approximately 45% vol. In one particular embodiment of the invention the alcohol content is increased more rapidly from 45% vol to 75% vol. The concentration of alcohol in the eluent is then increased at a substantially constant rate from 75% vol, until it reaches 95% vol. The liquid leaving the column is collected in fractions. This liquid may be analysed after leaving the column by the use of an in-line spectrophotometer.

In another preferred embodiment of the invention, an extract containing bioactive components is obtained from grape skins. The extract contains the following bioactive components in order of hydrophobicity: stilbenes (including resveratrol), flavonols (including quercetin and myricetin), catechins and phenolic acids. The stilbenes are very strongly hydrophobic, whilst the phenolic acids are relatively hydrophilic.

To ensure maximum recovery of stilbenes, whilst avoiding excessive losses of phenolic acids, alcohol is added to the extract until the resultant extract/alcohol mixture is approximately 58% alcohol. This ensures that the phenolic acids and the catechins will not be adsorbed when in contact with an adsorbent. The extract/alcohol mixture is then passed through a first adsorbent column, preferably packed with polystyrene-divinyl benzene beads as adsorbent. The stilbenes and flavonols are selectively adsorbed on the first column whilst the remaining extract/alcohol mixture, containing catechins and phenolic acids passes through the first column. Alcohol is then removed from the remaining extract/alcohol mixture to reduce the alcohol content to approximately 7% to 10%, and the de-alcoholised mixture is passed through a second adsorption column, preferably containing polystyrene-divinyl benzene adsorbent, where the catechins and phenolic acids are adsorbed.

Each of the adsorbent columns is then fed with an eluent mixture of water and alcohol. The concentration of alcohol in the eluent is gradually increased, and fractions containing different bioactive components are collected. The concentration of alcohol in the eluent for the first column is increased at a substantially constant rate, preferably from about 50% to about 96% alcohol. The eluent for the second column is also increased at a substantially constant rate, preferably from about 15% to 35% alcohol.

Figure 11:
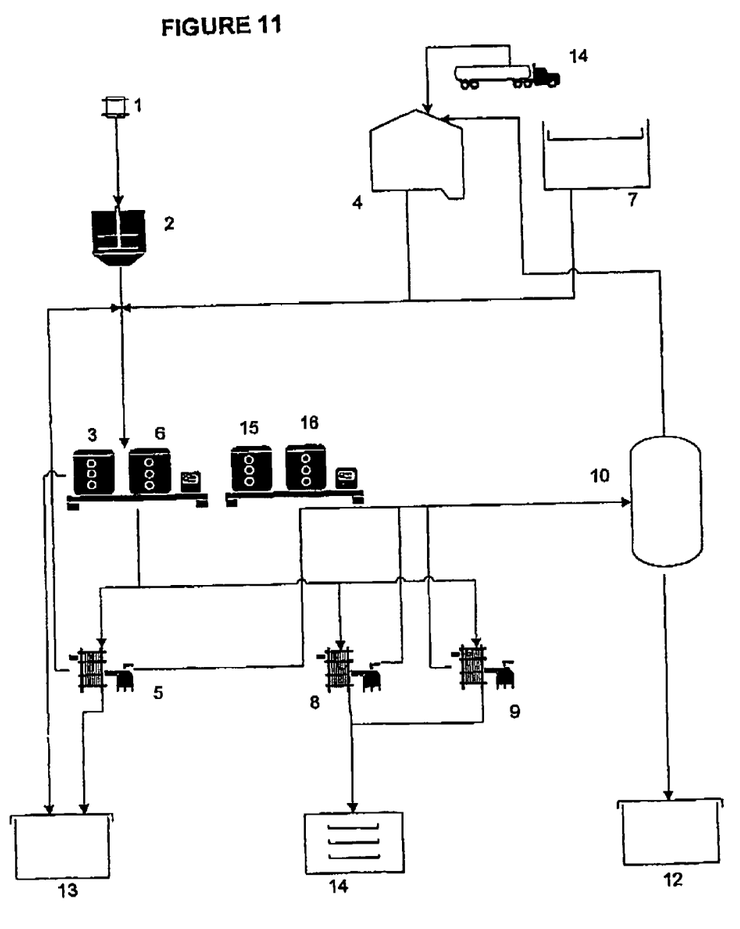
FIG. 11 is a schematic diagram of a plant for carrying out one embodiment of the process of the invention. Note that the number of evaporate in the process is directly related to the number of bioactive component fractions to be recovered.

FIG. 11 is a schematic diagram of a plant suitable for carrying out a preferred embodiment of the process according to the invention. As shown in the diagram, a raw plant material extract is fed from an extractor (1) to a stirred tank (2). The extract is then loaded to a first column (3), along with ethanol from the ethanol tank (4) and water from water tank (7). Relatively hydrophobic compounds are adsorbed on an adsorbent in column (3), whilst relatively hydrophilic compounds pass through column (3) to ethanol recovery evaporators (5), which remove most of the ethanol. The removed ethanol is returned to the ethanol tank (4) via distillation unit (10). The de-alcoholised extract is loaded to a second column (6) where the hydrophilic components are adsorbed on an adsorbent. Further ethanol is removed from the treated extract discharged from the second column (6) in ethanol recovery evaporators (5), and the treated extract is then discharged for disposal, or if desired, further treatment or use (13).

A mixture of ethanol from ethanol tank (4) and water from water tank (7) is then added to each of the columns (3, 6). The proportion of alcohol to water is increased over time so as to elute the bioactive components as separate fractions. The separate factions are each sent to a product evaporator (8, 9) for removal of alcohol and water to concentrate the bioactive component. The number of product evaporators (8, 9) will depend upon the number of fractions containing bioactive components; ideally each fraction will go to a separate product evaporator. The alcohol and water removed from the bioactive component is sent to a distillation unit (10) where alcohol is recovered and returned to the ethanol tank (4). The remaining components from the distillation unit are sent to distillation waster (12). The concentrated bioactive components obtained from the product evaporators (8, 9) are then freeze dried in freeze drier (11) for storage and transportation. In an alternative embodiment, (not shown), the concentrated bioactive components may be combined with an oil base, rather than freeze dried.

It should be noted that there might be some losses of ethanol during the process; for this reason make-up ethanol (14) may need to be added to the ethanol tank (4) from time to time. Preferably there are four columns (3, 6, 15, 16) being loaded and/or eluted at any one time.

EXAMPLE

The following example illustrates the present invention in further detail, it being understood, however, that this example should by no means be construed as defining the scope of the invention Orange peel was obtained and shaved using suitable shaving equipment. The shavings were then stored in 200 litre drums and stored at −18° C. for two days. The drums were then stored at 5° C. for a further two days in preparation for the extraction.

The shavings were sliced in a slicer with a 4 mm gap. Sliced pieces were then fed into a counter current diffusion extractor at a rate of 1.2 kg per 5 minutes, and extracted with hot water. The juice generated was pumped via a heat exchanger to 60 litre tanks. The resulting juice was at an approximate temperature of 25° C. Sixty grams of citric acid were then added to the base of each empty juice tank to provide approximately 1 gram of citric acid litre of juice. The addition of citric acid ensured a low pH level ensuring that the pH in each tank did not exceed 3.8. Ascorbic acid was also added to the base of each tank, to result in the overall addition of 100 ppm of ascorbic acid to all juice in this batch.

The juice was partially depectinisied by adding 10 mls of Vinozym 3 XL per 50 litre juice. Each tank was then pasteurised at 93° C. for 90 seconds. The depectinised juice was then fed to a self desludging centrifuge at the rate of 220 litres per hours to further clarify the juice.

The centrifuged juice (total 152.4 kg) was then fed into gravity feed column containing a 20 litre bed of polystyrene-divinyl benzene copolymer XAD 16. The bed was prepared by washing respectively with the following solutions (i) 2 bed volume of water (ii) 1 bed volume of 2% Sodium Hydroxide (ii) 2 bed volume of water (iv) 1 bed volume of citric acid and (v) 2 bed volume of water.

The clarified juice was then passed through the column at a rate of 1 bed volume (20 litres) per hour. The column was flushed with 2 bed volumes of deionised water and a further 2 bed volumes of 10% vol ethanol in water mixture. This treatment with dionised water and alcohol solution was to remove sugar and acid from the column as well as a proportion of the weakly hydrophobic phenolic compounds adsorbed onto the adsorbent, without removing a substantial portion of the Limonoid and Flavonoid components.

Figure 1:
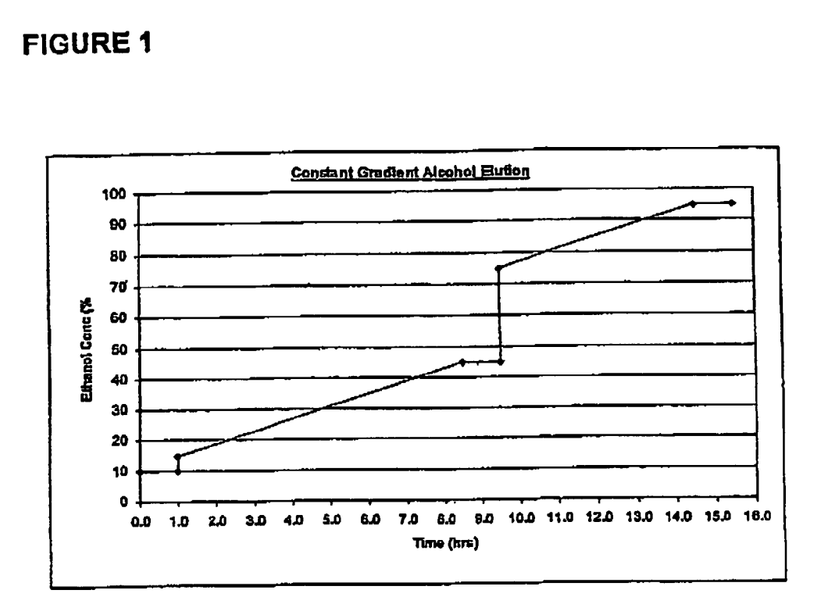
FIG. 1 illustrates a graph of ethanol concentration in eluent mixture over time.

A mixture of ethanol and demineralised water was then was passed through the column at a continuous rate of one bed volume per hour resulting in a feed rate of 20 litres per hour. The initial concentration of ethanol in the mixture was 10 vol % this was increased to 15 vol % ethanol. The concentration was then increased at a constant rate of 10 vol % for each 2.5 bed volumes of eluent. This meant that the alcohol concentration increased from 15 vol % to 45 vol % over 7.5 hours. The concentration was then kept at 45 vol % for an hour. After this period the concentration of ethanol in the mixture was rapidly increased to 75 vol % ethanol. Over the next 5 hours the concentration was increased constantly from 75 vol % to 95 vol % ethanol. An example of the change in ethanol concentration in the mixture entering the column over time during the adsorption is illustrated in FIG. 1. The mixture leaving the column was then passed through an in-line spectrophotometer to determine the amount of recoverable components in each of the fractions. The liquid leaving the column was then collected in equal fractions which were sequentially number 1 to 111, and represented the total eluate over the course of the experiment.

Figure 2:
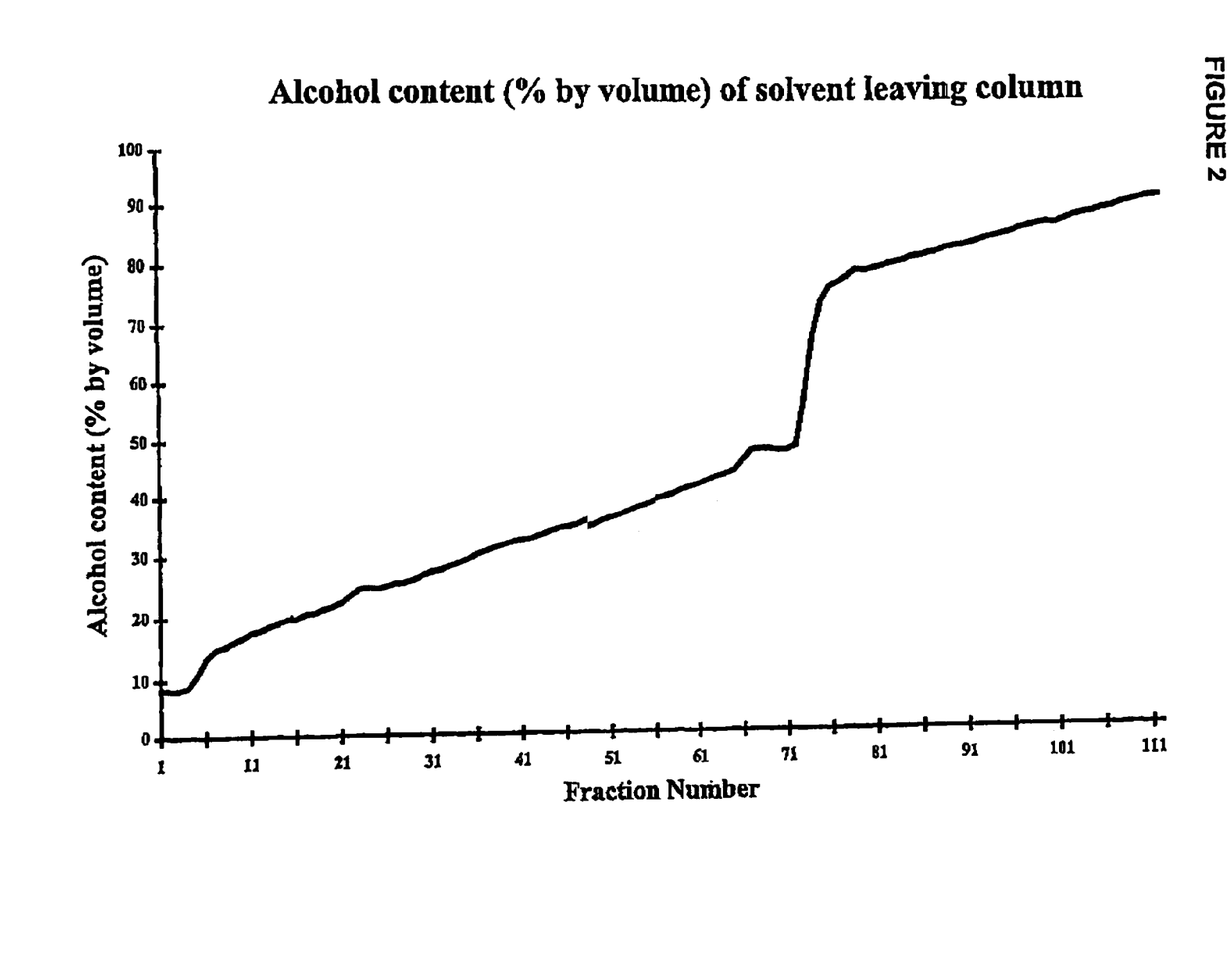
FIG. 2 illustrates a graph of alcohol concentration varying with fraction number.

The alcohol concentration leaving the column was then analysed. Alcohol volume (as a percentage of liquid leaving the column) plotted against the fraction number is illustrated in FIG. 2.

Figure 3:
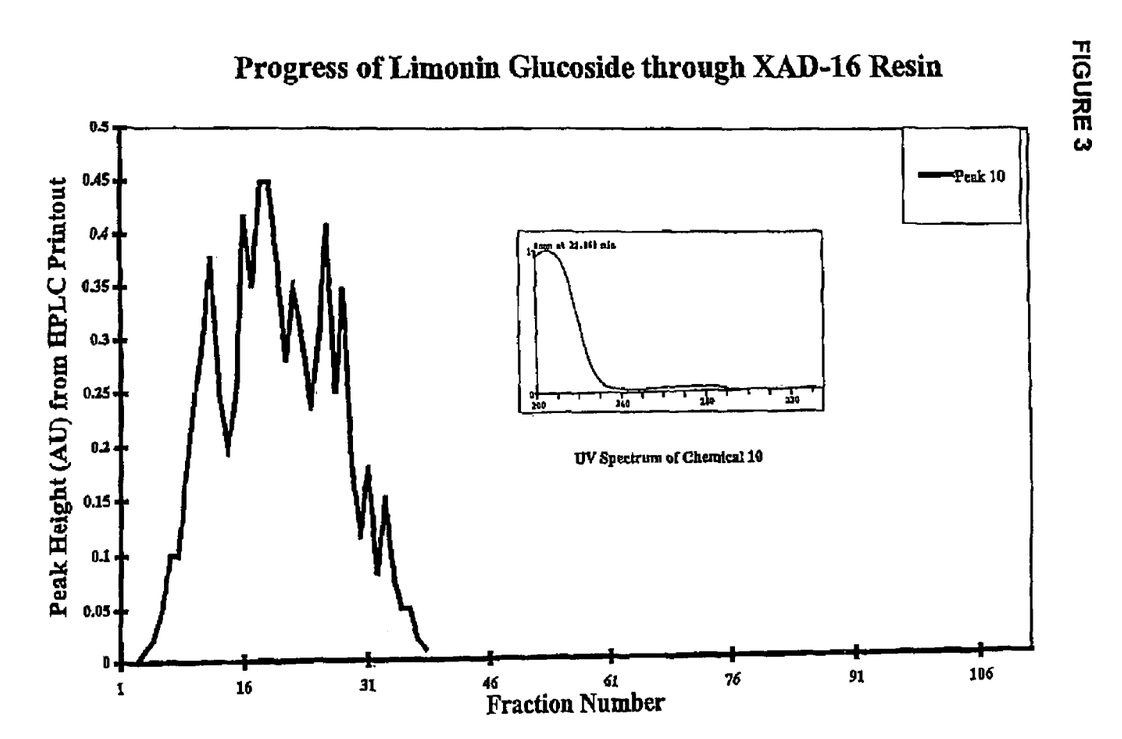
FIG. 3 is a chromatographic analysis illustrating the presence of Limonin Glucoside in fractions collected.
Figure 4:
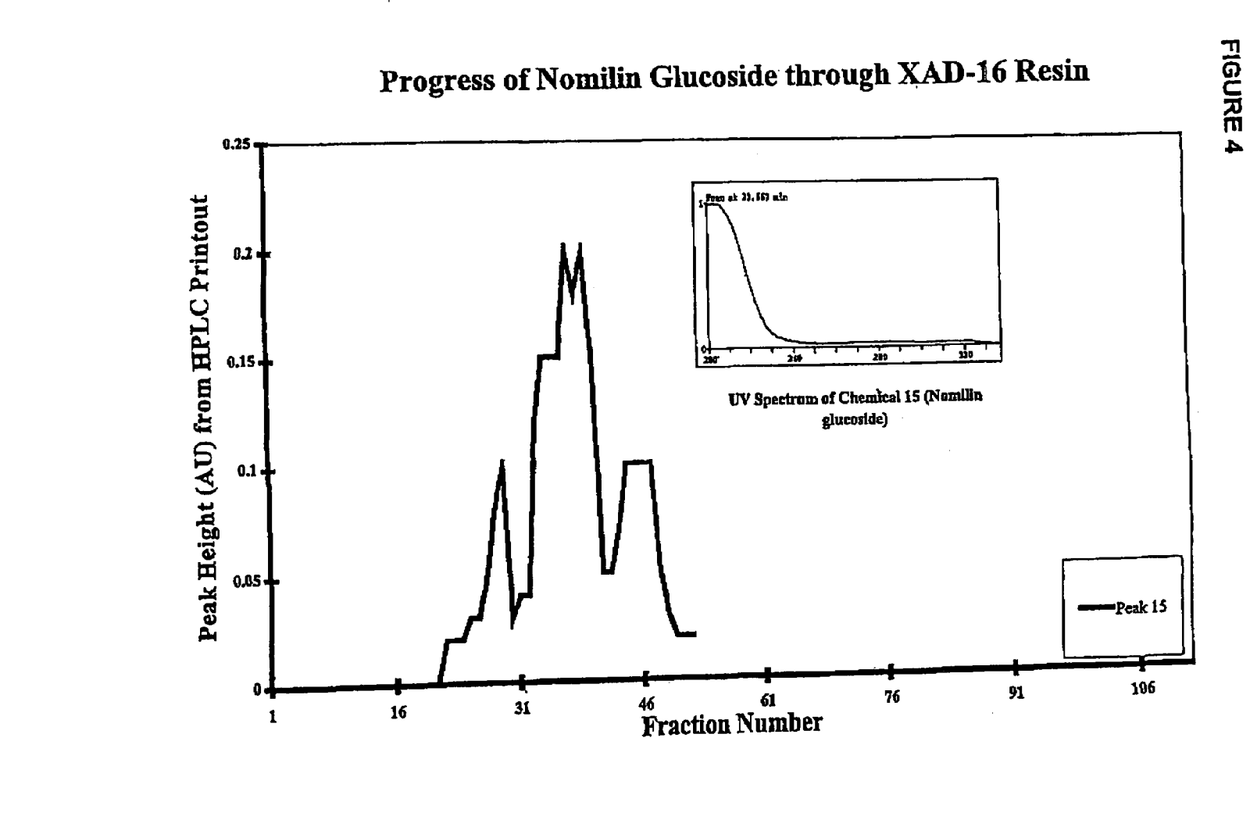
FIG. 4 is a chromatographic analysis illustrating the presence of Nomilin Glucoside in fractions collected.
Figure 5:
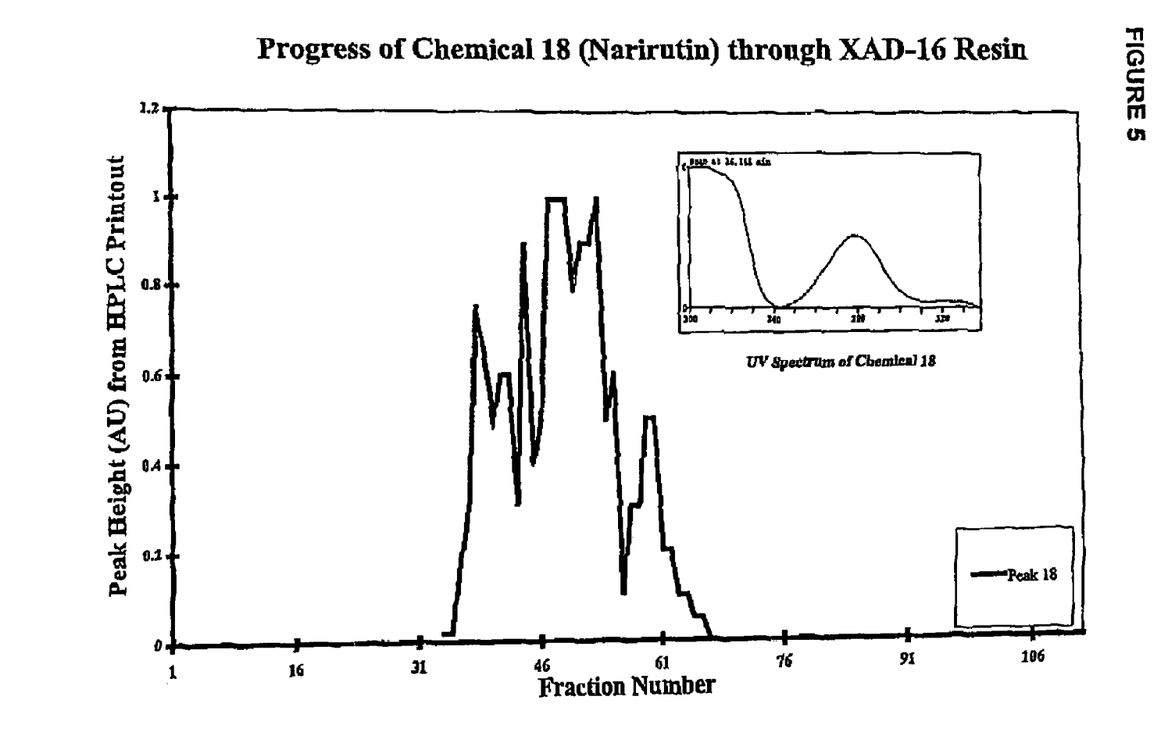
FIG. 5 is a chromatographic analysis illustrating the presence of the Flavanone Glycoside Narirutin in fractions collected.
Figure 6:
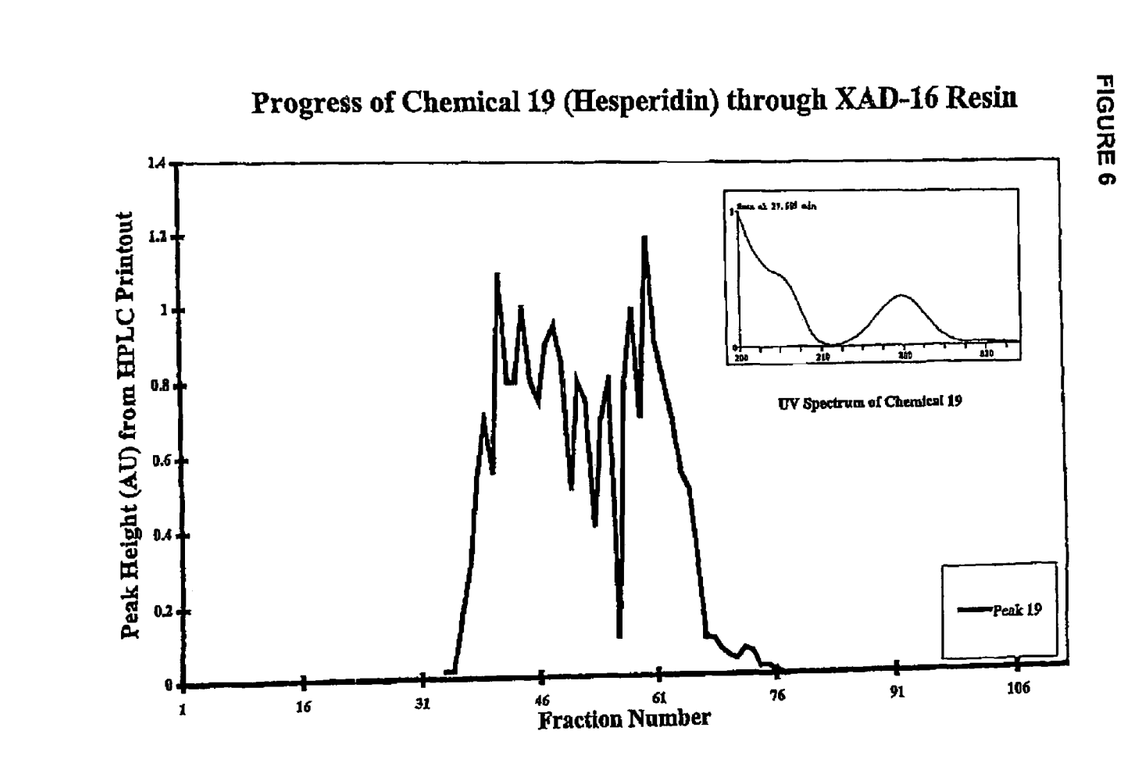
FIG. 6 is a chromatographic analysis illustrating the presence of the Flavanone Glycoside Hesperidin in fractions collected.
Figure 7:
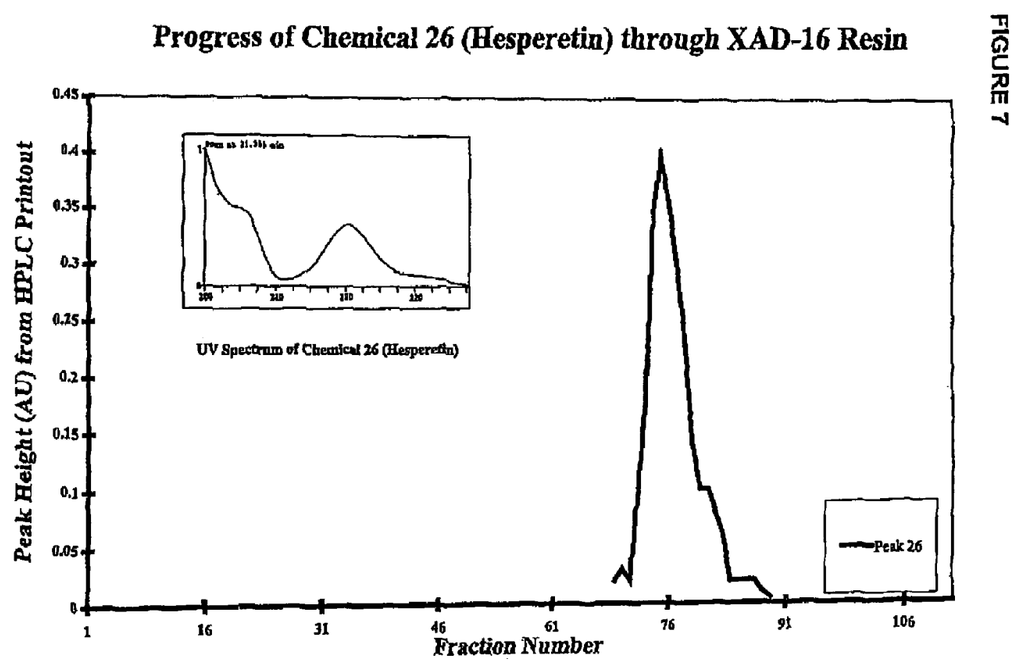
FIG. 7 is a chromatographic analysis illustrating the presence of the Flavanone Aglycone Hesperetin in fractions collected.
Figure 8:
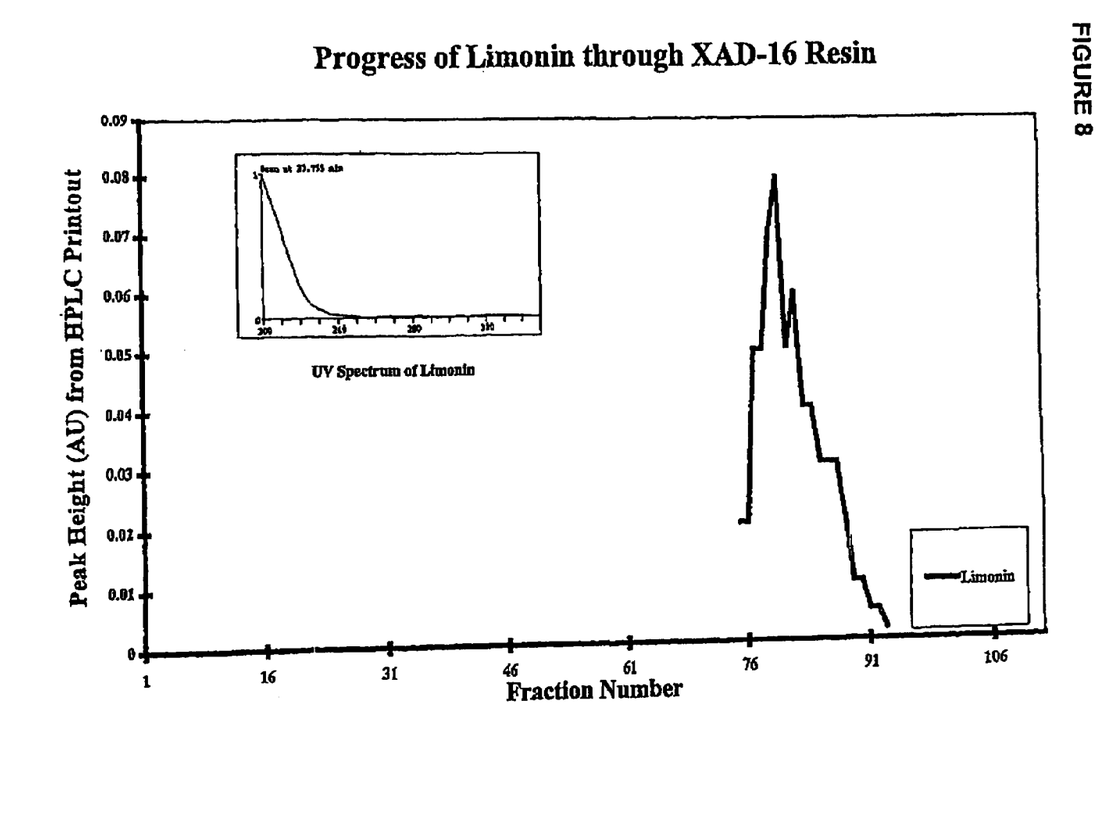
FIG. 8 is a chromatographic analysis illustrating the presence of Limonin in fractions collected.
Figure 9:
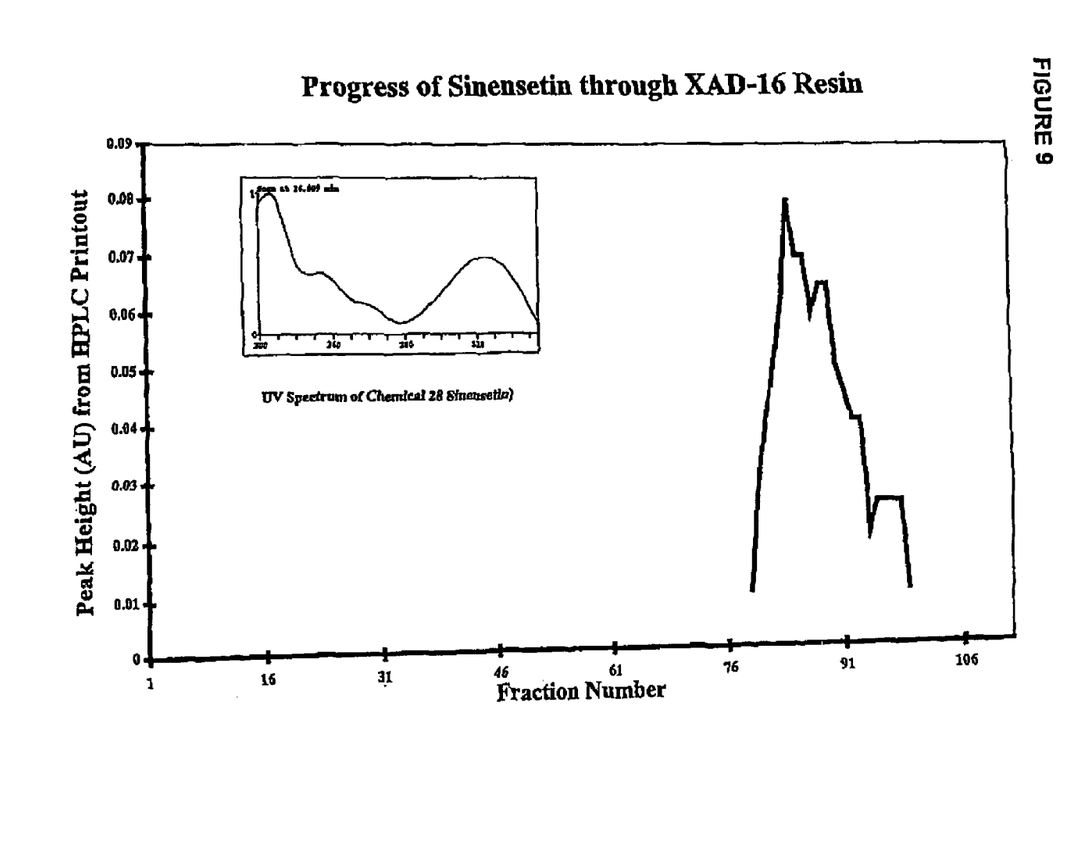
FIG. 9 is a chromatographic analysis illustrating the presence of the Polymethoxylated Flavone Sinensetin in fractions collected.
Figure 10:
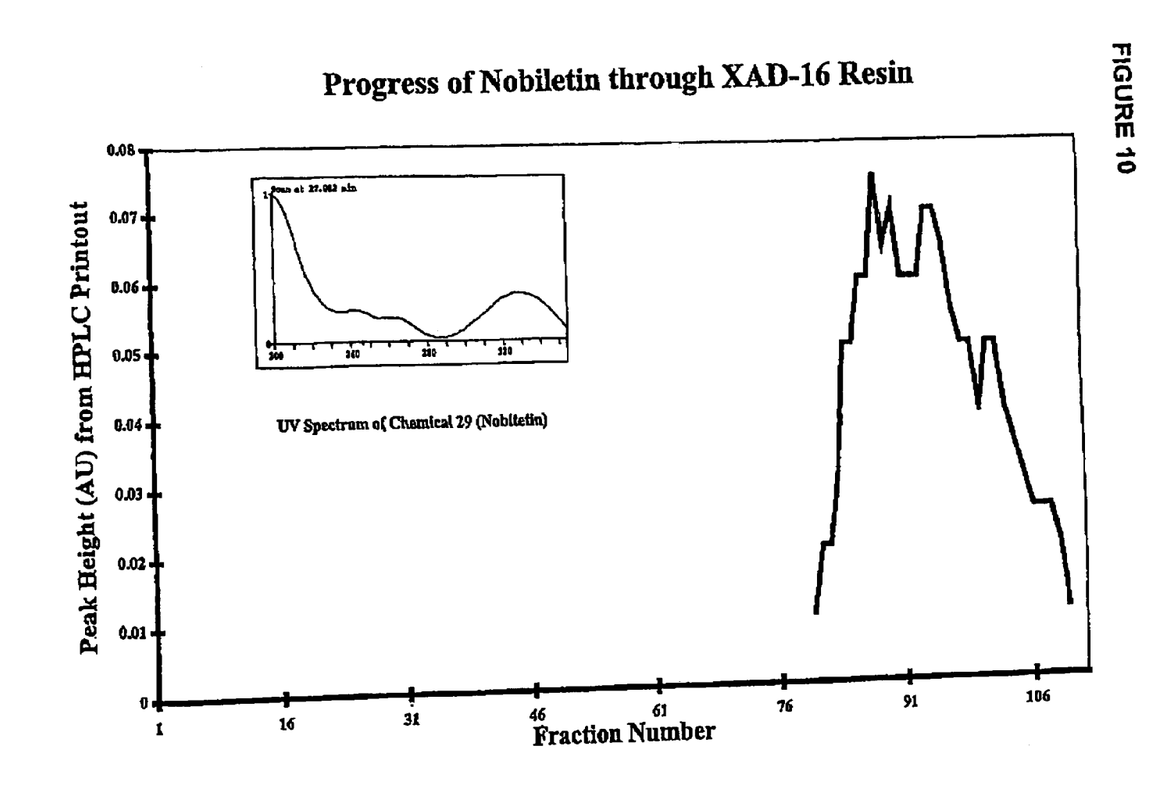
FIG. 10 is a chromatographic analysis illustrating the presence of the Polymethoxylated Flavone Nobiletin in fractions collected.

The fractions were analysed using high-pressure liquid chromatography (HPLC) and results are set out in FIGS. 3 to 10. The components were identified by comparing the relative peak heights with standards from those compounds having the same retention time and ultra violet spectra. These figures illustrate the chromatographic analysis of a variety of components present in fractions leaving the column. FIG. 3 illustrates a chromatographic analysis of Limonin Glucoside in fractions leaving the column. FIG. 4 illustrates a chromatographic analysis of Nomilin Glucoside in fractions leaving the column. FIG. 5 illustrates a chromatographic analysis of Nariutin in fractions leaving the column. FIG. 6 illustrates a chromatographic analysis of Hesperidin in fractions leaving the column. FIG. 7 illustrates a chromatographic analysis of Hesperetin leaving in fractions leaving the column. FIG. 8 illustrates a chromatographic analysis of Limonin in fractions leaving the column. FIG. 9 illustrates a chromatographic analysis of Senensetin in fractions leaving the column. FIG. 10 illustrates a chromatographic analysis of Nobiletin in fractions leaving the column.

Each of the fractions leaving the column was then treated by evaporating the alcohol to leave a concentrated solution including the desired components. After the evaporation step, the remaining components were freeze dried for storage.

The total amount of target components recovered from 1 kg of Orange albedo was determined by adding together the amounts from all fractions to determine the following compositions—

Limonin glucoside; 282 mg

Nomilin glucoside (including Nomilinic acid): 177 mg

Narirutin:>80 mg

Hesperidin:>80 mg

Sinensetin: 11 mg

Other compounds considered to be polymethoxylated flavones:>11 mg

These compositions are for all fractions together. The components are concentrated in different fractions, for example Limonin glucoside was eluted in the first four fractions.

These numbers are indicative only and were produced after a single trial.

It is to be understood that various additions, alterations and/or modifications may be made to the parts previously described without departing from the ambit of the invention.

The invention claimed is:

1. A process for selectively extracting bioactive components from a raw material extract derived from vegetable matter, including the steps of:
   (a) passing said raw material extract through a passageway containing an adsorbant whereby at least some of the components to be extracted are adsorbed on said adsorbent;
   (b) subsequently passing through said passageway an eluent mixture substantially containing water and alcohol whereby the concentration of alcohol in the eluent is increased at a substantially constant rate from 15 vol percent to 95 vol percent during at least those periods when the components are being eluted; and
   (c) sequentially collecting an eluate in fractions corresponding to the presence of the extracted components.

2. A process for selectively extracting bioactive components from a raw material extract derived from vegetable matter; including the steps of:
   (a) combining said raw material extract with sufficient alcohol to ensure at least one bioactive component will not be adsorbed when the combined raw material and alcohol are passed through a first passageway containing adsorbent;
   (b) passing said combined raw material extract and alcohol through a first passageway containing an adsorbent whereby at least some of the components to be extracted are adsorbed on to said adsorbent;
   (c) reducing the alcohol component of the combined raw material extract and alcohol to less than 15 vol percent;
   (d) passing the combined raw material extract and remaining alcohol through a second passageway containing an adsorbent whereby remaining components to be extracted are adsorbed on said adsorbent;
   (e) subsequently passing through said first passageway an eluent mixture substantially containing water and alcohol wherein the concentration of alcohol in the eluent is increased at a substantially constant rate from 50 vol percent to 95 vol percent during at least those periods when the components are being eluted;
   (f) subsequently passing through said second passageway an eluent mixture substantially containing water and alcohol wherein the concentration of alcohol in the eluent is increased at a substantially constant rate from 15 vol percent to 35 vol percent during at least those periods when the components are being eluted; and
   (g) sequentially collecting from each passageway an eluent in fractions corresponding to the presence of the boiactive components.

3. A process according to claim 1 wherein the rate of increase of alcohol concentration of the eluent is greater between 45 vol percent to 75 vol percent alcohol.

4. A process according to claim 2 in reduction of the alcohol component of the combined raw material extract and alcohol to less than 15 vol percent is achieved by removing alcohol in an evaporator.

5. A process according to claim 1 or claim 2 wherein said adsorbent is polystyrene-divinyl benzene.

6. A process according to claim 1 or claim 2 wherein said alcohol is ethanol.

7. A process according to claim 1 or claim 2, including the additional step of processing said fractions further by evaporating the alcohol to yield a further concentrated form of the extracted component.

8. A process according to claim 1 or claim 2 in which the vegetable matter is selected from citrus fruit and the bioactive components are limonoid glucosides, flavanones and polymethoxylated flavones.

9. A process according to claim 1 or claim 2 in which the vegetable matter is sugar cane and the bioactive components are phenolic acids and hydroxy flavones.

10. A process according to claim 1 or claim 2 in which the vegetable matter is selected from apples, potatoes, or a mixture of apples and potatoes, and the boiactive components are phenolic acids, proanthocyanidins, adroxyflavones and flavonols.

11. A process according to claim 1 or claim 2 in which the vegetable matter is grapes and the bioactive components are flavonols, stilbenes, proanthocyanidins, phenolic acids and anthocyanins.

* * * * *